(12) United States Patent
Wilson et al.

(10) Patent No.: US 6,544,195 B2
(45) Date of Patent: Apr. 8, 2003

(54) TISSUE OF FOREIGN BODY EXTRACTOR

(76) Inventors: Joseph F. Wilson, 6054 W. Tucson Estates Pkwy., Tucson, AZ (US) 86713; Riley K. Wilson, 17701 Spain Dr., Anchorage, AK (US) 99516; Frances R. Wilson, 7175 Oline Cir., Anchorage, AK (US) 99507

( * ) Notice: Subject to any disclaimer, the term of this patent is extended or adjusted under 35 U.S.C. 154(b) by 0 days.

(21) Appl. No.: 09/798,527

(22) Filed: Mar. 2, 2001

(65) Prior Publication Data

US 2001/0034495 A1 Oct. 25, 2001

Related U.S. Application Data

(60) Provisional application No. 60/186,935, filed on Mar. 4, 2000.

(51) Int. Cl.$^7$ .................................................. A61B 5/00
(52) U.S. Cl. ....................... 600/564; 600/217; 600/235; 600/567
(58) Field of Search ............................... 600/564, 567, 600/217, 235

(56) References Cited

U.S. PATENT DOCUMENTS

| 5,437,266 A | | 8/1995 | McPherson et al. | ........ 600/217 |
| 5,439,478 A | * | 8/1995 | Palmer | ........ 606/205 |
| 5,573,496 A | | 11/1996 | McPherson et al. | ........ 600/217 |
| 5,662,683 A | | 9/1997 | Kay | ........ 600/232 |
| 5,762,069 A | * | 6/1998 | Kelleher et al. | ........ 600/564 |
| 5,843,017 A | * | 12/1998 | Yoon | ........ 604/22 |

* cited by examiner

Primary Examiner—A. Michael Chambers
(74) Attorney, Agent, or Firm—Birdwell, Janke & Durando, PLC

(57) ABSTRACT

A tissue or foreign body extractor. A coil member is provided, and in one embodiment of the invention, is disposed within the lumen of a needle. The needle includes one or more cutting edges for cutting into tissue located in the body, a core of the tissue being received in the lumen. The coil member is connected to an elongate shaft that extends through the lumen of the needle for remotely operating the coil member Turning the shaft threads the coil member into the core. Thereafter, retracting the shaft tears the core at its juncture with the remaining mass of tissue or foreign body, and withdraws the core from its locus in the body.

15 Claims, 2 Drawing Sheets

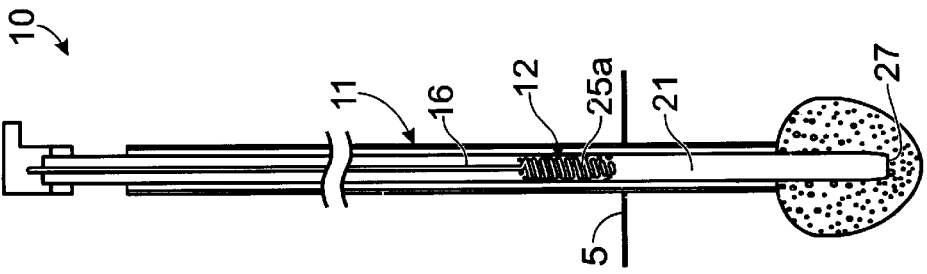
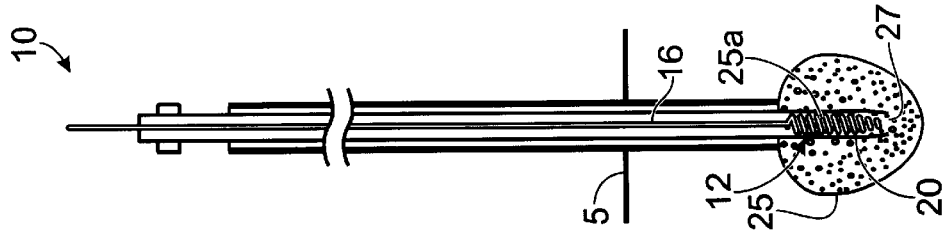
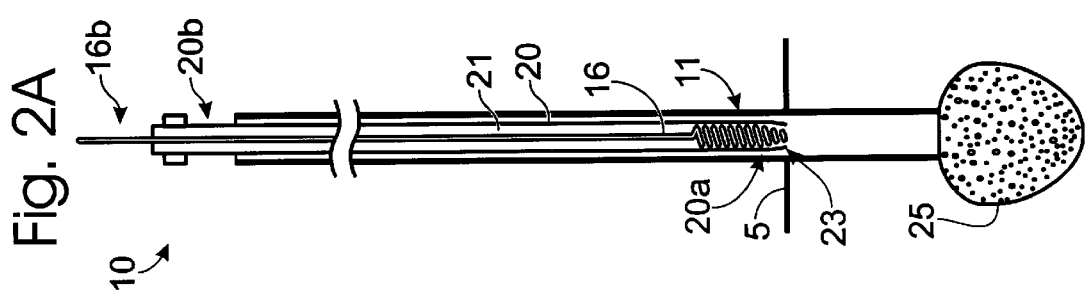

TISSUE OF FOREIGN BODY EXTRACTOR

The present application claims the benefit of the inventor's provisional application Ser. No. 60/186,935, filed Mar. 4, 2000 incorporated by reference herein in its entirety.

BACKGROUND OF THE INVENTION

The present invention relates to a tissue or foreign body extractor, such as for use in a biopsy needle or flexible endoscope.

It is a common surgical procedure to cut and remove internal body tissue by remotely manipulating cutting and grasping elements passed through devices such as catheters or endoscopes ("remotely operated devices") The remotely operated devices are typically introduced into the patient's body through incisions or body orifices.

In a core biopsy, for example, a needle having a lumen therethrough and one or more cutting edges is employed as the cutting element. The cutting edges of the needle are advanced into the tissue, cutting a core of the tissue that is received in the lumen.

Often, a separate grasping element is used in the remotely operated devices that employs closable jaws. However, such grasping elements are relatively bulky and require additional space for opening the jaws. It is desirable for the remotely operated devices to be as slender as possible, to minimize invasiveness and to permit threading the remotely operated devices through narrow body passageways such as the bronchial air passages or the esophagus. Moreover, providing separate opposably moving parts increases manufacturing cost and decreases reliability.

To address these problems, the grasping element may be replaced with suction provided to the end of the remotely operated device. The suction is communicated through the device to the tissue, dislodging the tissue and conveying the tissue through the device. However, providing suction requires a pump which increases the cost and complexity of the procedure, and the suction is difficult to modulate or control without the use of additional costly hardware.

Accordingly, there is a need for a tissue or foreign body extractor that provides for minimum size, decreased cost and complexity, and increased reliability and operational control.

SUMMARY OF THE INVENTION

The tissue or foreign body extractor of the present invention solves the aforementioned problems and meets the aforementioned needs by providing, in a biopsy embodiment of the invention, a coil member disposed within the lumen of a needle. The needle includes one or more cutting edges for cutting into tissue located in the body, a core of the tissue being received in the lumen. The coil member is connected to an elongate shaft that extends through the lumen of the needle for remotely operating the coil member. Turning the shaft threads the coil member into the core. Thereafter, retracting the shaft tears the core at its juncture with the remaining mass of tissue and withdraws the core from its locus in the body.

In a foreign body extractor embodiment of the invention, the needle is preferably omitted, and the coil member is anchored to the foreign body for withdrawing the foreign body.

In yet another embodiment of the invention, the coil screw member is provided in an endoscope according to either of the embodiments mentioned above.

Therefore, it is a principal object of the present invention to provide a novel and improved tissue or foreign body extractor.

It is another object of the present invention to provide a tissue or foreign body extractor that provides for minimum size, to permit introduction into or through narrow body passageways.

It is yet another object of the present invention to provide a tissue or foreign body extractor that provides for decreased cost and complexity, such as in manufacturing and during operation.

It is still another object of the present invention to provide a tissue or foreign body extractor that provides for increased reliability, including device and operation reliability It is a further object of the present invention to provide a tissue or foreign body extractor that provides for increased ease of controlling of the device.

The foregoing and other objects, features and advantages of the present invention will be more readily understood upon consideration of the following detailed description of the invention, taken in conjunction with the following drawings.

BRIEF DESCRIPTION OF THE DRAWINGS

FIG. 2A is a side section of a tissue or foreign body extractor according to the invention, shown in a position preliminary to entry into the body.

FIG. 2B is a side section of the tissue or foreign body extractor of FIG. 2A shown cutting into the tissue or foreign body.

FIG. 2C is a side section of the tissue or foreign body extractor of FIGS. 2A and 2B, shown with a coil member according to the invention partially threaded into the tissue or foreign body.

FIG. 2D is a side section of the tissue or foreign body extractor of FIGS. 2A–2C, shown with the coil member threaded into the tissue or foreign body.

FIG. 2E is a side section of the tissue or foreign body extractor of FIGS. 2A–2D, shown with the coil member being retracted with a dislodged piece of the tissue or foreign body.

DETAILED DESCRIPTION OF A PREFERRED EMBODIMENT

Figure 1:
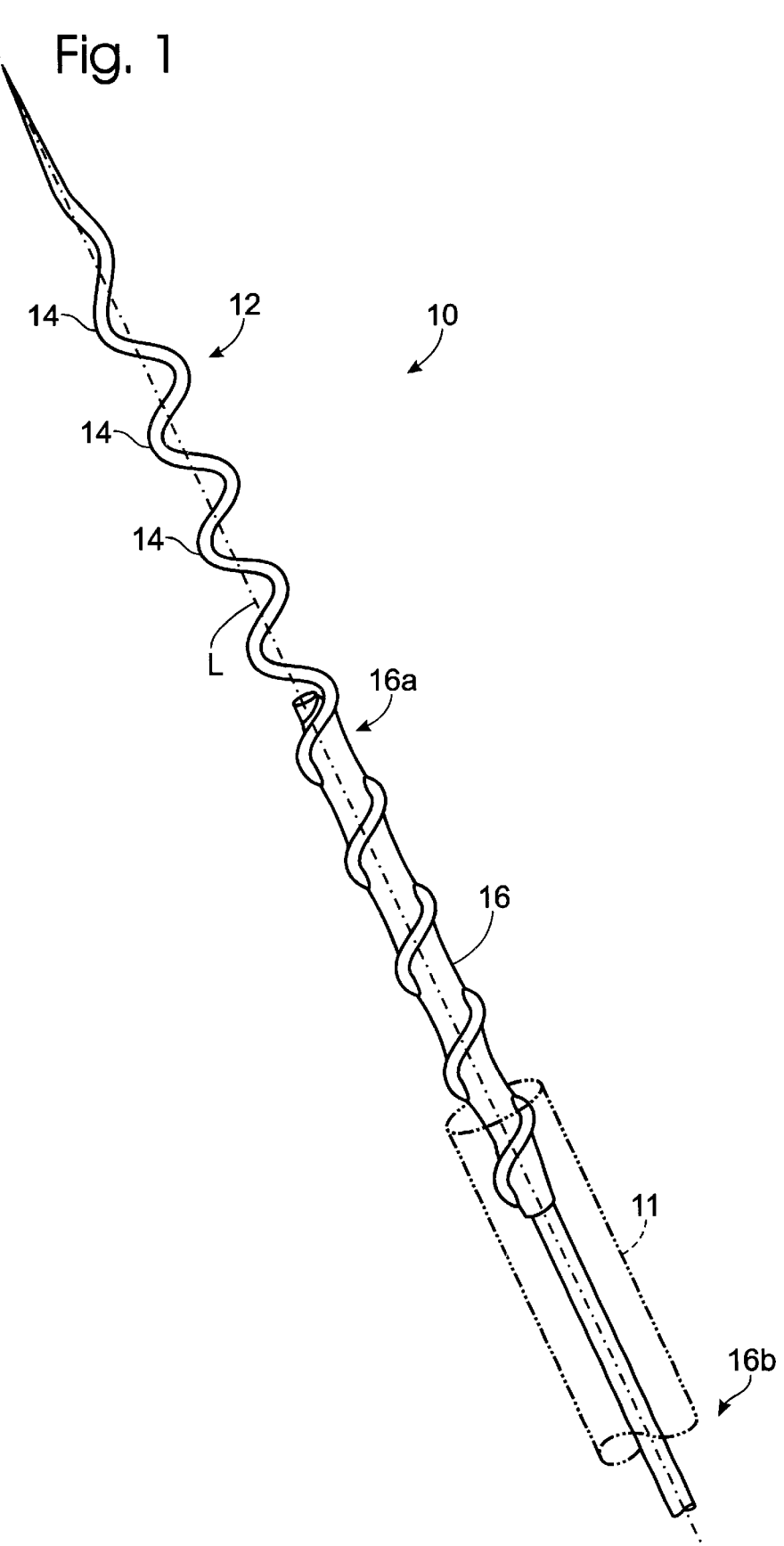
FIG. 1 is a pictorial view of a tissue or foreign body extractor according to the present invention.

Referring to FIG. 1, a tissue or foreign body extractor 10 according to the present invention is shown. The extractor 10 is shown in a foreign body extractor embodiment of the invention, but may be used as shown for extracting any tissue or foreign body that is located inside the body. The extractor is generally employed to anchor to the tissue or foreign body, and withdraw the entire mass or a piece thereof from its locus in the body.

The extractor is typically employed in conjunction with a remotely operated surgical device 111 such as a catheter or endoscope. For purposes herein, a catheter is distinguished from an endoscope in that the endoscope includes an optical transmitter, such as an optical fiber, so that the endoscope permits illumination or viewing as well as remote operation of surgical devices. A significant consequence of this distinction is that endoscopes must have a larger diameter to provide space for the optical transmitter, and it may therefore be more critically important in an endoscope to minimize the size of surgical devices used therein, to minimize this diameter and to permit a given surgical procedure.

The extractor 10 includes a grasping element that includes a coil member 12 having a plurality of helical coils 14, wherein a single coil is defined by a 360 degree rotation about the elongate axis "L" of the coil member. The coil member 12 is connected to the distal end (16a) of an elongate shaft 16 having its elongate axis aligned with the axis "L." The coil member may be integrally or joinedly connected to the shaft, the latter such as by thermal or ultrasonic welding, brazing or bonding, e.g., with an adhesive. The shaft extends sufficiently from the coil member to permit access to the shaft for remote operation thereof, i.e., for turning the shaft about its axis "L" and for withdrawing the shaft distally along this axis. The shaft is preferably sufficiently long in relation to its thickness or diameter that it is flexible, so that it is suitable for use in a flexible catheter or endoscope, though this is not essential to the invention.

Turning to FIGS. 2A and 2B, a biopsy embodiment of the invention is shown, wherein the extractor 10 further includes a cutting element that includes a needle 20. As for the foreign body extractor embodiment, however, the extractor 10 may be used as shown for extracting any tissue or foreign body that is located inside the body.

A distal end 20a of the needle includes one or more cutting edges 23 for cutting or otherwise penetrating the tissue 25. The coil member 12 is disposed within a lumen 21 of the needle. The shaft 16 extends through the lumen 21 out the proximal end (20b) of the needle. In FIG. 2A, the extractor 10 has been inserted through a skin layer 5 and the remotely operated device 11 is shown in FIG. 2B as having been guided to a mass of tissue or foreign body 25.

Referring to FIG. 2C, the needle 20 is pressed or otherwise manipulated into the mass 25 so that a core 25a thereof is taken up in the lumen 21. The core 25a still however generally attached to remaining portions of the tissue 25 at a juncture 27, The coil member 12 is turned by turning the shaft 16, and is thereby threaded into the core 25a a sufficient amount for grasping the core, such as shown in FIG. 2D.

Referring to FIG. 2E, the coil member 12 is next withdrawn by pulling the shaft 16. This action tears or otherwise dislodges the core 25a from its site at the juncture 27, and withdraws the core.

A biopsy can be accomplished without forming a cylindrical core; however it is an outstanding advantage of the invention to be able to provide a core in this configuration. Alternatively, the embodiment shown in FIG. 1 may be used for biopsy by omitting the needle and simply tearing an irregular piece of the tissue penetrated by the coil member from a larger mass of tissue. Omitting the needle is believed to be especially advantageous in conjunction with use of the extractor in an endoscope, where as mentioned previously, minimizing device size may be critical.

Employed as described above, the coils 14 are preferably formed of wire having a circular cross-section of constant diameter. As shown in FIG. 1 for example, the coil member 12 may be formed of a helical wire coil or compression spring. The diameter and length of the coil member, and the spacing between the coils, are preferably optimized for the procedure and type of tissue or foreign body for which the extractor is used. In endoscopic procedures for extracting foreign bodies from bronchi, a preferred coil member has about a 2 mm outside diameter, is about 1.5 cm long, and has 2.5 turns per cm. For the same procedure in the esophagus, a preferred coil member has about a 2.5 mm outside diameter, is about 1.5 to 2 cm long and has about 1.6 turns per cm.

The shaft 16 is preferably substantially cylindrical and the coils 14 are wrapped around the shaft, wherein at least one of the coils is bonded to the shaft. The coils 14 may alternatively be provided in the form of screw threads projecting from the shaft, so that the piece 25a may be dislodged and conveyed by simply by turning the shaft.

It is to be recognized that, while a particular tissue or foreign body extractor has been shown and described as preferred, other configurations could be utilized, in addition to configurations already mentioned, without departing from the principles of the invention.

The terms and expressions which have been employed in the foregoing specification are used therein as terms of description and not of limitation, and there is no intention of the use of such terms and expressions of excluding equivalents of the features shown and described or portions thereof, it being recognized that the scope of the invention is defined and limited only by the claims which follow

What is claimed is:

1. An extractor for extracting tissue or a foreign body, comprising:

a coil member having a plurality of helical coils;

a shaft connected to said coil member, said shaft having an elongate axis; and a needle having a lumen therethrough coaxially disposed with respect to said shaft, said shaft being free to remotely translate said coil member relative to said needle along said axis.

2. The extractor of claim 1, wherein said helical coils have a substantially circular cross-section of a substantially constant diameter.

3. The extractor of claim 1, wherein at least one of said coils is disposed around said elongate shaft.

4. The extractor of claim 1, wherein said needle has a distal end having at least one cutting edge.

5. The extractor of claim 1, wherein said coil member is disposed within said lumen.

6. The extractor of claim 5, wherein said needle has a proximal end, and wherein said needle and said shaft are cooperatively adapted so that at least a proximal end of said coil member may be moved from being within said lumen to being outside said proximal end of said needle, for withdrawing the tissue or foreign body from said needle.

7. An extractor for extracting tissue or a foreign body, comprising:

a coil member having a plurality of helical coils; and a shaft connected to said coil member, said shaft having an elongate axis; and an endoscope having a lumen therethrough coaxially disposed with respect to said shaft, said shaft being free to remotely translate said coil member relative to said needle along said axis.

8. An extractor for extracting tissue or a foreign body, comprising:

a coil member having a plurality of helical coils; and a flexible shaft having an elongate axis, said shaft being connected to said coil member and being free to remotely translate said coil member along said axis.

9. The extractor of claim 8, wherein said shaft is free to remotely turn said coil member about said axis.

10. An extractor for extracting tissue or a foreign body, comprising:

a needle having a lumen therethrough and adapted at a distal end thereof for pressing into the tissue or foreign body;

a coil member adapted at a distal end thereof for threading into the tissue or foreign body; and an elongate shaft at least partially disposed within said lumen connected to said coil member for remote operation of said coil member.

11. The extractor of claim 10 wherein said distal end has at least one cutting edge.

12. The extractor of claim 11 wherein said needle and said shaft are cooperatively adapted so that at least a distal end of said coil member may be moved from being within said lumen to being outside said distal end of said needle, for threading into the tissue or foreign body disposed thereat.

13. The extractor of claim 10, wherein said needle has a proximal end, and wherein said needle and said shaft are cooperatively adapted so that at least a proximal end of said coil member may be moved from being within said lumen to being outside said proximal end of said needle, for withdrawing the tissue or foreign body from said needle.

14. The extractor of claim 11, wherein said needle has a proximal end, and wherein said needle and said shaft are cooperatively adapted so that at least a proximal end of said coil member may be moved from being within said lumen to being outside said proximal end of said needle, for withdrawing the tissue or foreign body from said needle.

15. The extractor of claim 12, wherein said needle has a proximal end, and wherein said needle and said shaft are cooperatively adapted so that at least a proximal end of said coil member may be moved from being within said lumen to being outside said proximal end of said needle, for withdrawing the tissue or foreign body from said needle.

* * * * *